United States Patent [19]

Rodenberg et al.

[11] 4,038,297

[45] July 26, 1977

[54] HIGH MOLECULAR WEIGHT MONOCARBOXYLIC ACIDS AND OZONIZATION PROCESS FOR THEIR PREPARATION

[75] Inventors: Herbert G. Rodenberg; Charles E. Patton, both of Cincinnati, Ohio

[73] Assignee: Emery Industries, Inc., Cincinnati, Ohio

[21] Appl. No.: 566,891

[22] Filed: Apr. 10, 1975

Related U.S. Application Data

[63] Continuation-in-part of Ser. No. 361,205, May 17, 1973, abandoned.

[51] Int. Cl.$^2$ .............................................. G07C 51/32
[52] U.S. Cl. .................................... 260/413; 44/7.5; 106/8; 106/10; 106/19; 106/27; 106/243; 106/268; 252/35; 252/39; 252/41; 252/56 R; 252/56 S; 260/23 XA; 260/45.85 R; 260/410.6; 260/410.7; 260/419; 424/172; 424/365
[58] Field of Search .................. 260/413, 23 XA, 419; 106/268, 270, 8, 27

[56] References Cited

U.S. PATENT DOCUMENTS

| | | | |
|---|---|---|---|
| 2,813,113 | 11/1957 | Goebel et al. | 260/406 |
| 2,819,279 | 1/1958 | Brown et al. | 260/413 |
| 3,383,393 | 5/1968 | Peck et al. | 260/413 |
| 3,389,084 | 6/1968 | Bartlett et al. | 252/39 |
| 3,676,489 | 7/1972 | Ellis et al. | 260/413 |
| 3,691,219 | 9/1972 | Bousseley | 260/410.7 |
| 3,691,233 | 9/1972 | Ellis et al. | 260/413 |
| 3,696,134 | 10/1972 | Washecheck | 260/413 |
| 3,702,345 | 11/1972 | Fermald et al. | 260/683.15 D |
| 3,745,033 | 7/1973 | Hutchison | 106/268 |

*Primary Examiner*—Winston A. Douglas
*Assistant Examiner*—P. E. Konopka
*Attorney, Agent, or Firm*—Gerald A. Baracka; John D. Rice

[57] ABSTRACT

High molecular weight carboxylic acids are provided. The mixed acid products of this invention typically contain a high percentage of aliphatic straight-chain monocarboxylic acids containing 22 or more carbon atoms. The monocarboxylic acids are obtained by the ozonization of high molecular weight α-olefins under controlled conditions. Using this ozonization process it is possible to obtain mixed acid products wherein the predominant acids contain 22 to 35 carbon atoms. An additional feature of this invention is the ability to obtain mixed acid products wherein acids having an odd number of carbon atoms are present in significantly larger amounts than acids having an even number of carbon atoms.

12 Claims, No Drawings

HIGH MOLECULAR WEIGHT MONOCARBOXYLIC ACIDS AND OZONIZATION PROCESS FOR THEIR PREPARATION

CROSS REFERENCES

This is a continuation-in-part of our copending U.S. application Ser. No. 361,205, filed May 17, 1973, now abandoned.

BACKGROUND OF THE INVENTION

High molecular weight aliphatic straight-chain monocarboxylic acids and derivatives thereof are used in various polish formulations for shoes, leather, furniture, floors and automobiles, in carbon paper, in paper sizing compositions and in coatings. They are also useful as dispersing additives, lubricating agents, mold release agents and the like. In the past high molecular weight acids were typically obtained by treatment of natural products such as carnauba wax, beeswax, candelilla wax and montan wax. Montan wax (obtained from lignite and other bitumin-enriched soft coals by extraction with organic solvents) has been a particularly useful source for high molecular weight aliphatic acids since about 70% of the crude extract is a wax component composed primarily of free acids (25%) and mixed esters of long-chain acids and alcohols (65%).

The monocarboxylic acids can be obtained from montan wax using saponification procedures, however, the chromic acid oxidation process developed in Germany is used for commercial production of montan wax acids. Montan wax acids are primarily mixed aliphatic monocarboxylic acids containing from about 8 to 40 carbon atoms. The bulk of the acids contain an even number of carbon atoms and fall within the $C_{22-34}$ carbon content range with the $C_{26}$, $C_{28}$ and $C_{30}$ acids generally comprising about 30–45% by weight of the total acids. The acid distribution can vary depending on the particular type or source of montan wax. The composition of German montan wax, for example, differs appreciably from that of American montan wax. In all cases, however, the predominant monocarboxylic acids obtained by the chromic acid oxidation of montan wax have an even number of carbon atoms.

It would be extremely useful to have a synthetic source available for the production of high molecular weight aliphatic straight-chain monocarboxylic acids in approximately the same carbon content range as montan wax acids. In the past there has been no completely satisfactory method for producing such acids. The various known processes all have shortcomings and are not acceptable for commercial operations. For example, oxidation of α-olefins or mixtures of α-olefins such as are available from the polymerization of ethylene produce monobasic acids, however, large amounts of undesirable low molecular weight acids, polymeric residue and other undesirable low molecular weight acids, polymeric residue and other undesirable by-products are formed. Nitric acid oxidation of α-olefins produces undesirable nitro by-products in addition to giving poor yields of the desired acids. The carboxylation of α-olefins with carbon monoxide using acid catalysts followed by hydrolysis also gives low yields due to the poor selectivity of the reaction. Procedures such as those described in U.S. Pat. Nos. 2,293,649 and 3,842,106 can also be employed to produce high molecular weight acids, however, these are branched-chain acids.

It would be highly useful and advantageous if a process were available to produce high molecular weight aliphatic straight-chain acids in good yield and high purity, especially if the process were readily adaptable to commercial operations.

SUMMARY OF THE INVENTION

We have now found that high molecular weight α-olefins can be safely and conveniently ozonized at temperatures above 50° C to obtain useful high molecular weight aliphatic straight-chain monocarboxylic acid compositions containing about 70% by weight or more acids having 22 or more carbon atoms. When the olefins ozonized above about 50° C and preferably between about 60° and 85° C in a participating solvent, which is a monocarboxylic acid containing from about 4 to about 13 carbon atoms, it is possible to obtain good yields of mixed acid products which contain less than 20% acids having fewer than 22 carbon atoms. With olefin feeds containing at least 60% by weight α-olefins of the formula $R'CH=CH_2$ where R' is an alkyl radical containing 20 to 48 carbon atoms the resulting acid compositions contain about 70% or more $C_{22-35}$ monocarboxylic acids where the ratio of odd to even carbon content acids is greater than about 1.5:1. Preferably the ratio of odd to even carbon content acids will range from about 1.75:1 to about 4:1. The ratio of olefin to participating solvent useful for conducting the present ozonization process ranges between about 2:1 to about 1:10.

DETAILED DESCRIPTION

The present invention is directed to the preparation of high molecular weight monocarboxylic acids which are typically mixtures wherein the predominant acids are aliphatic straight-chain monocarboxylic acids containing 22 or more carbon atoms. These mixed acid products are obtained by the ozonization of high molecular weight α-olefins.

Olefins utilized in the ozonization process contain between about 22 and 60 carbon atoms. They are preferably α-olefins, however, internal (non-vinyl) olefins may be present in limited amounts. α-Olefins should constitute about 60% or more of the olefin feed and best results are obtained when 75% or more of the olefins are of the vinyl type, that is, α-olefins. The presence of internal olefins is to be avoided whenever possible if the production of branched-chain and low molecular weight acids as well as keto and hydroxyl by-products is to be minimized.

Especially useful for the production of high molecular weight monocarboxylic acids in accordance with this invention are olefin feeds containing at least 60% by weight α-olefins of the formula $R'CH=CH_2$ wherein R' is an alkyl radical containing from 20 to 48 carbon atoms. Olefin feeds meeting these requirements may be obtained by the polymerization of ethylene, such as for example, the addition of ethylene to an aluminum alkyl. Such chain growth reactions where ethylene is inserted between aluminum and one of the alkyl groups are described in the literature. Olefins of a predetermined average size are obtained by terminating the growth reaction at a predetermined point and then displacing the long alkyl group. The length of the alkyl group will be dependent on the reaction conditions and amount of ethylene charged. Numerous variations of these processes are available to shift distribution in favor of preferred olefins or to otherwise bring about compositional variations. Where olefins having a narrow molecular weight distribution are desired it may be necessary to fractionally distill, solvent extract or otherwise treat the resulting olefin products prior to ozonization.

The above-described olefins or olefin mixtures are contacted with ozone in a suitable participating reaction medium, preferably at a temperature above the titering point of the olefin/solvent reaction mixture, and then cleaved and oxidized to obtain the high molecular weight monocarboxylic acids. In general the reaction procedure involves distinct steps of ozonization followed by scission and oxidation of the formed ozonides. The procedures employed for the various steps of the reaction are not critical and known methods can be used such as those described in U.S. Pat. No. 2,813,113. The entire reaction or any of the individual steps can be conducted as batch, continuous or semi-continuous operations at atmospheric, subatmospheric or superatmospheric pressure. The pressure is not ciritical and may be varied throughout the ozonization and oxidation steps, however, it is most convenient to conduct the reaction at essentially atmospheric pressure.

The first step of the process comprises reacting the olefin or olefin mixture with ozone. The ozone gas may be prepared by means of an ozone generator. It is perferable in carrying out the ozonization to mix the ozone with a carrier gas such as argon, neon, nitrogen, oxygen, air, carbon dioxide and mixtures thereof. In this way it is possible to achieve more uniform reaction rates and to more effectively meter and control the ozone concentration in the reaction vessel. Excellent results are obtained when the carrier gas is oxygen or a mixture of oxygen with air or carbon dioxide and when the gas mixture contains from about 0.1 to about 15% by weight ozone and more preferably from about 1 to 5% ozone.

The olefin is contacted with the ozone in a suitable reactor or absorber to obtain the olefin ozonide. The olefin and solvent may be fed to the reactor separately or may be combined in a mixing tank and this mixture charged. The amount of ozone admitted to the reactor can be determined by ultraviolet analysis, thermal conductivity or other known methods. When a continuous process is used the olefin, usually dissolved in the participating reaction medium, and ozone-containing gases are fed at rates in relation to each other so the essentially all of the ozone is reacted in one pass through the absorber and only small amounts of ozone remain in the carrier gas. The amount of ozone utilized upon passage through the reaction zone can be determined by scrubbing the effluent gases with aqueous potassium iodide and titrating the free iodine formed with sodium thiosulfate. The feed rate of olefin is also maintained so that the olefin absorbs the maximum amount of ozone, that is, all the unsaturation is essentially reacted. If the process is conducted as a batch operation the olefin to be reacted is generally combined with the participating solvent in the reaction vessel and ozone passed through the liquid using a gas dispersing means. Vigorous agitation is desirable to maintain acceptable contact of the gas and olefin in the reactor.

A stoichiometric amount of ozone is generally employed if efficient contact of olefin and ozone is maintained, however, in certain systems, particularly batch processes, it may be desirable to add a slight excess of ozone to insure that all the olefin is reacted. If ozone is present in the effluent gases it may be useful to recycle these gases to more completely utilize the ozone or the gases may be passed through a scrubber containing aqueous sodium hydroxide or sodium thiosulfate to remove the ozone and prevent contamination of the atmosphere.

Numerous refinements and modifications of the ozonization procedure are possible and will be apparent to those skilled in the art. The method of charging the olefin and ozone or ozone-containing gases is not critical and various prodcedures can be employed depending on whether a batch or continuous process is used. Similary, many variations for metering and determining the concentration of the materials in the reactor and feed streams and for recycling the olefin and/or ozone gases are possible.

The olefin ozonide formed during the ozonization step is next reacted with oxygen under conditions which promote scission and oxidation of the ozonide to the acid products. The scission and oxidation steps may be conducted simultaneously or as separate and distinct operations. This is achieved in conventional equipment employing either batch or continuous procedures, the only requirement being that the olefin ozonide be intimately mixed with oxygen and that some means to be provided for controlling the temperature. The olefin ozonides decompose readily at elevated temperatures and they are easily oxidized to the desired acid products, however, the decomposition may be accelerated and better controlled by the use of a suitable catalyst. Useful catalysts for this purpose include alkali or alkaline earth metal compounds such as sodium hydroxide, potassium hydroxide, barium hydroxide, or the like. After an inital period of heating required to initiate the oxidation reaction the reaction generally continues without additional heating, in fact, cooling is necessary to control the exothermic reaction.

An amount of gaseous oxygen sufficient to completely oxidize the ozonide is required. While pure oxygen may be advantageously employed other oxygen containing gases such as mixtures of oxygen with argon, helium, neon or nitrogen may also be used for this purpose, however, the gas mixtures should contain at least 20% by weight oxygen. An amount of oxygen from about 1 to about 4 moles of oxygen per mole of olefin is required by larger amounts may be employed as desired to speed the process, insure complete oxidation and improve yields. If suitable equipment is available to recycle unused oxygen very high molar excesses, in the order of 10 to 100 moles oxygen per mole starting material, can be employed without adversely affecting the economics of the process.

As previously indicated the design of the apparatus used to carry out the scission and oxidation of the ozonides can vary so long as good contact between the liquids and gases is provided. Agitation, such as stirring and rocking, can be employed or the materials can be caused to flow counter-currently in continuous equipment. The efficiency of contacting the materials is important since the time required for splitting and oxidizing the ozonides is highly dependent thereon. In most instances this phase of the reaction is substantially complete in from about ½ to about 20 hours.

While catalysts are not necessary to bring about the scission and oxidation of the ozonide they may be desirable to accelerate these reactions and their use is often advantageous. Synergistic combinations of catalytic agents may be used. Useful materials which may be added to the ozonide mixture prior to subjecting it to oxidation and which serve as catalytic agents include the alkali and alkaline earth metal hydroxides and various metal compounds including salts of Group VIII metals, preferably iron, cobalt and nickel, and other compounds of these and other metals such as manganese. The chlorides, sulfates and carboxylates of these metals are useful as are the oxides and hydroxides. The metal compounds may be used individually or combinations of two or more metal compounds may be useful. The amount of the total catalyst will range from about 0.01% to about 2% by weight of the total reaction mixture. Manganese compounds and particularly manganese salts of $C_{2-16}$ carboxylic acids have been found particularly effective for this purpose, especially when used in conjunction with alkali metal hydroxides.

A cooling means sufficient to handle the requirements of the reactor should be provided to control the reaction exotherm once the oxidation has been initiated. In continuous processes it may be useful to recycle partially split (oxidized) ozonides into a stream of fresh ozonides prior to the scission and oxidation stages or a fresh stream of the olefin ozonides may be continuously fed into a vessel or receptacle which contains partially split and oxidized ozonides. This provides a convenient way to continuously dilute the ozonide making it possible to more readily control the reaction exotherm and also has other advantages such as obtaining more efficient oxidation utilizing small amounts of oxygen and improving the yields of the product. The reaction may also be controlled by increasing the ratio of participating solvent to olefin.

To achieve the useful acid products of this invention it is required that a solvent capable of participating in the reaction be employed. Participating solvents useful for the present invention are monocarboxylic acids containing from about 4 to about 13 carbon atoms. The useful participating solvents preferably have boiling points sufficiently high to withstand the elevated reaction temperatures employed, thus avoiding excessive losses of solvent due to volatilization and other complications. Especially useful acids for this invention contain from about 6 to 12 carbon atoms and include, for example, caproic, caprylic, pelargonic, capric and lauric acids. Mixtures of acids within the specified carbon content ranges and particularly mixtures of monocarboxylic acid which contain at least 80% by weight $C_{6-12}$ acid may be conveniently employed in the process. While straight-chain acids are typically employed due to their ready availability, branched-chain acids are also useful including the α-alkyl branched acids and iso-acids. Pelargonic acid and mixtures of acids containing 50% or more pelargonic acid are especially useful participating solvents for this invention.

In conducting the process the weight ratio of the olefin to participating solvent may range from about 2:1 to about 1:10. Especially useful results are obtained at weight ratios between about 1:1 and 1:3. The olefin and participating solvent may be combined prior to contacting with the ozone or at least part of the solvent may be added continuously or incrementally at any stage prior to the oxidation and scission step.

In addition to the use of a participating solvent, the temperatures at which the ozonization is conducted is also important and should be maintained above about 50° C and preferably above the titering point of the olefin, participating solvent and olefin ozonide mixture. Temperatures in the ozonization step will therefore usually range between about 60° C and about 85° C, however, they may go as high as 100° C. By conducting the reaction at these elevated temperatures the reaction mixture is maintained in a fluid state and this facilitates dispersion of the gaseous ozone and allows intimate contact of the gases with the olefin so that uniform reaction rates and complete absorbtion of ozone is achieved.

The ability to safely conduct the ozonization at temperatures about 50° C and still obtain a safe and controllable reaction is unexpected in view of the reported instability of olefin ozonides in the literature. Numerous reports of spontaneous decomposition of olefin ozonides are available, however, it is possible and necessary with the present process to ozonize the high molecular weight olefins at temperature of 50° C to as high as 100° C when the ozonization is conducted in the participating solvents mentioned. However, even as is the practice with ozonizations conducted at much lower temperatures, for example, at 0° C or below, precautions should be taken with this process to avoid isolated hot spots and high concentrations of olefin ozonides in the process equipment and lines. The usual precautions, however, will suffice for this purpose.

The usual temperature employed in the scission and oxidation steps of the process will range between about 75° and 145° C. If distinct steps are employed for the scission and oxidation the same temperatures may be employed, however, it is more customary to conduct the oxidation at slightly higher temperatures than the scission. Temperatures between about 85° and 105° C are normally employed to cleave the olefin ozonides whereas it is preferred that the oxidation be conducted at temperatures between about 100° and 125° C. Uniform and controllable scission and oxidation are obtained when these temperature limits were observed.

Since the ozonization process does not significantly reduce the chain length of the olefin, the composition of the acid products obtained is primarily related to the makeup of the α-olefin. If the α-olefin to be ozonized has a narrow molecular weight distribution the acid products will correspondingly show little compositional variation, however, if the α-olefin mixture is comprised of olefins having a wide variation in molecular weight, the acid products will also have a wide compositional range. When olefin feeds of the type described above are used the resulting mixed acids will be predominantly aliphatic straight-chain monocarboxylic acids containing less than 30 weight percent acids having fewer than 22 carbon atoms and less than 20% by weight acids having greater than about 35 carbon atoms with $C_{22-35}$ acids constituting 55% by weight or more of the mixed acid product. More preferably the acid compositions will contain less than about 20 weight percent acids having fewer than 22 carbon atoms, greater than 70 percent $C_{22-35}$ acids and less than about 10% acids containing more than 35 carbon atoms.

An additional aspect of the invention, as pointed out earlier, is the ability to obtain a larger proportion of acids containing an odd number of carbon atoms in the chain. The exact ratio will be controlled by the reaction conditions employed, however, it is primarily governed by the amount of α-olefin present in the olefin feed. The presence of olefinic materials having unsaturation in other than terminal positions will significantly reduce this ratio and is therefore undesirable if high yields of odd carbon content acids is desired. When high molecular weight α-olefins of the type previously described are used as the feed, the ratio of odd carbon content acids to even carbon content acids in the $C_{22-35}$ product will range from about 1.5:1 upwards to as high as 10:1, however, it is generally from about 1.75:1 to about 4:1.

The mixed acid products of this invention are useful in a variety of applications. They are typically used in formulations where montan wax, carnauba wax, beeswax or other natural or synthetic waxes are presently used and can be substituted in whole or in part therefor. While the acids are in themselves quite useful derivatives of these acids such as the esters, soaps, ester/soaps, amides and the like can also be employed and are sometimes advantageous where minor modifications in the mixed acid waxes are desired. These derivatives also find utility as substitutes for the above-mentioned natural waxes as well as other synthetic and natural wax products. For example, the mixed acids of this invention and derivatives thereof are useful in liquid, paste nd wax polish formulations for shoes and boots, leather, floors and automobiles; in printing inks and for carbon paper; in paper coatings; in paints and varnishes; in candles and other wax products such as crayons; in water proofing formulations; for lubricating purposes including grease formulations and lubricating agents for textile finishing and plastic extrusion; in cosmetic formulations; as mold release agents; as dispersants; in adhesives; and the like.

The following examples illustrate the invention more fully, however, they are not intended as a limitation on the scope thereof. Modifications and variations are possible and will be evident to the person skilled in the art. In these examples all parts, percentages and ratios are given on a weight basis unless otherwise indicated.

EXAMPLE I

A reactor was charged with a mixture of 300 gms of a mixed olefin containing 60% high molecular weight α-olefins (Gulf $C_{30+}$ alpha-olefin fraction, m.p. 160°-167° F, having 78 weight percent $C_{30}$ and higher olefins) and 300 gms pelargonic acid (Emfac 1202 pelargonic acid). A stream of oxygen containing 3% ozone was continuously bubbled in below the surface of the liquid at a rate of 24 SCFH at 4 psig so that approximately 35 gms ozone was being charged per hour. The temperature of the absorber was maintained at about 75° C with vigorous agitation to insure intimate contact with the ozone and the progress of the reaction was followed by analyzing the off gases. The ozonolysis was terminated when ozone absorption dropped below 15%.

The ozonides thus formed were oxidatively cleaved by the dropwise addition of the mixture over a period of about 90 minutes into a vessel containing 100 gms pelargonic acid and 0.75 gms sodium hydroxide. The reaction mixture was vigorously agitated and maintained at about 95° C while bubbling in a stream of oxygen containing 1% ozone at a rate of 2.4 SCFH. When the addition was complete, stirring was continued for an additional 90 minutes while bubbling in the $O_3/O_1$ mixture. The ozone generator was then turned off. Manganese acetate tetrahydrate (1.5 gms) was added and the temperature of the reaction mixture raised to 120° C while bubbling in pure oxygen with stirring. After 3½ hours the oxidation reaction was complete and the mixed oxidation product was stripped of pelargonic acid by heating to 230° C while pulling a vacuum of 25 torr on the system. In the final stages of the stripping operation the vacuum was reduced to 3 torr. A 100% yield (based on olefin charge) of the high molecular weight mixed monocarboxylic acids was obtained. The acid value of the final product was 123.5 and the product had an equivalent weight of 454.

EXAMPLE II

To obtain the mixed acid products of this invention on a larger scale, equal parts of $C_{30+}$ α-olefin and pelargonic acid were fed into the top section of a countercurrent absorber while a stream of oxygen and carbon dioxide containing approximately 1.5-2% ozone was fed into the bottom section. The rates of flow of the $O_3/O_2$ gas stream and the olefin feed were adjusted so that the $C_{30+}$ α-olefin absorbed as much ozone as possible in passing through the absorber and so that all but trace amounts of ozone were removed from the oxygen. The temperature in the absorber was maintained in the range 65°-85° C. The effluent gases were scrubbed with water to remove organic vapors and particulate matter and then passed through a catalytic furnace where organic matter was oxidized to carbon dioxide and water. The gas was then dried and recycled.

The ozonide was removed from the bottom of the absorber and passed into a decomposition vessel containing a heel of pelargonic acid, 0.25% sodium hydroxide based on weight of ozonide and previously decomposed ozonide to serve as a diluent. The decomposition vessel was maintained at a temperature of 95° C while adding oxygen containing 1% ozone and the ozonide added over a 2 hour period. When the addition was complete the decomposition was continued for an additional 2 hours transferring to a reactor for oxidation. The oxidation was carried out at 120° C in the presence of manganese acetate tetrahydrate (0.1% level based on the $C_{30+}$ olefin) in an oxygen atmosphere. The time required for oxidation was 4 hours.

The mixed oxidation product was then stirred with 0.5% of 75% phosphoric acid for 15 minutes and an activated bleaching clay (Filtrol Grade No. 1) added with additional stirring. The mass was filtered to remove the manganese salts of phosphoric acid and the filter aid and then stripped of pelargonic acid under pressure using a Vigreaux column. Stripping was conducted at 230° C and during the final stages the pressure was reduced to 0.5 torr. The residue (identified as II-A) remaining after removal of the pelargonic acid was the mixed acid product which may be used as such or further purified by recrystallization from methanol, 2-nitropane, acetic acid or similar solvents.

1671 Grams of the mixed acid product were dissolved in 5000 mls glacial acetic acid by heating and stirring. When solution was complete the mixture was cooled to room temperature with agitation and then allowed to stand overnight. After filtering, washing with an acetic acid and air drying, 79.7% mixed acid product (identified as II-B) having an equivalent weight of 586 and a 7-8 Garder color was recovered.

Samples of the crude mixed acid product (II-A) and the product recrystallized from acetic acid (II-B) were analyzed by chromatography to determine the acid composition. The fatty acid composition was determined by gas-liquid chromatography of the methyl esters of the acids employing a modification of ASTM Test Method D-1983-64T. A Hewlett Packard Model 5750 chromatograph equipped with a 6 feet × ⅛ inch stainless steel column packed with 10% silicone rubber on 80-100 mesh Diatoport S was used. The instrument was programmed for an 8° C per minute temperature rise over the range 75°-333° C with a helium flow of 15 mls per minute and 50 psig. The products had the following compositional analysis:

| ACID (wt%) | II-A | II-B | ACID (wt%) | II-A | II-B |
|---|---|---|---|---|---|
| $C_7$ | 0.09 | — | $C_{26}$ | 3.19 | 3.08 |
| $C_8$ | 0.27 | — | $C_{27}$ | 9.76 | 11.57 |
| $C_9$ | 7.02 | 1.47 | $C_{28}$ | 2.74 | 2.83 |
| $C_{10}$ | 0.50 | 0.12 | $C_{29}$ | 9.12 | 12.54 |
| $C_{11}$ | 1.41 | 0.43 | $C_{30}$ | 1.28 | 1.72 |
| $C_{12}$ | 0.36 | 0.15 | $C_{31}$ | 8.12 | 10.35 |
| $C_{13}$ | 0.41 | 0.15 | $C_{32}$ | 1.32 | 1.29 |
| $C_{14}$ | 0.82 | 0.24 | $C_{33}$ | 6.06 | 8.13 |
| $C_{15}$ | 1.18 | 0.37 | $C_{34}$ | 0.50 | 0.89 |
| $C_{16}$ | 1.59 | 0.55 | $C_{35}$ | 4.42 | 6.00 |
| $C_{17}$ | 1.87 | 0.70 | $C_{36}$ | 0.23 | 0.58 |
| $C_{18}$ | 2.28 | 0.83 | $C_{37}$ | 3.37 | 4.37 |
| $C_{19}$ | 2.41 | 1.08 | $C_{38}$ | 0.41 | 0.49 |
| $C_{20}$ | 2.96 | 1.63 | $C_{39}$ | 2.19 | 3.17 |
| $C_{21}$ | 3.64 | 2.55 | $C_{40}$ | 0.50 | 0.21 |
| $C_{22}$ | 3.56 | 3.85 | $C_{41}$ | 2.09 | 2.03 |
| $C_{23}$ | 4.51 | 5.14 | $C_{42}$ | — | 0.06 |
| $C_{24}$ | 3.37 | 3.26 | $C_{43}$ | — | 1.04 |
| $C_{25}$ | 6.38 | 6.83 | | | |

The above data demonstrates the excellent results obtained with the present process and the ability to obtain high molecular weight aliphatic straight-chain monocarboxylic acids in good yields. While the crude product obtained simply by removing the solvent is of sufficient purity so that it is acceptable for most applications where high molecular weight acids are employed, it is possible to improve the products by recrystallization. Whereas the crude product contains nearly 75% $C_{22}$ and higher acids, and could be improved by further stripping, after recrystallizing from acetic acid the distribution of the high molecular weight acids is further improved and the percentage of $C_{22}$ and higher acids is increased to nearly 90%. Furthermore, it is seen that the ratio of odd to even carbon content acids in the $C_{22-35}$ range is increased from about 3:1 to nearly 4:1 in this manner. Similar high molecular weight acid compositions are obtained when other α-olefin feeds within the specified limits are employed. When a feed comprised essentially of $C_{24-32}$ α-olefins is used the distribution of resulting acids is quite narrow and high yields are obtained.

EXAMPLE III

To demonstrate further improvement in the mixed acids of this invention a crude acid product was bleached with ozone to improve the color. A 2-liter Morton flask was charged with about 1000 gms of mixed acid product having a Gardner color of about 12 which was prepared in accordance with the process described in Example II. The flask was fitted with an agitator, a reflux condenser and a fritted glass inlet tube below the surface of the acid. The mixture was heated to 100° C, vigorously agitated and ozone passed in from a Welsbach ozonator set for 7 psi oxygen, 115 volts and 0.04 cfm of gas. The bleaching was terminated after 90 minutes and the mixture slowly poured into 5 liters of methanol with stirring. Stirring was terminated when the mixture reached room temperature and allowed to stand overnight. The mixed acid product was recovered by filtering and allowed to air dry. A 79% recovery was obtained and the final product had an equivalent weight of 539, an acid value of 104, melting point of 77°-78° C and a 4+ Gardner color.

EXAMPLE IV

To demonstrate the utility of high molecular weight monocarboxylic acids of this invention a polish suitable for application to shoes and other leather articles was prepared by melting 4.5 gms of the crude high molecular weight monocarboxylic acid prepared following the procedure of Example II, 3.0 gms Carnauba (North Country No. 13), 1.5 gms microcrystalline wax (Petrolite C-1035) having a minimum melting point of 195° F and 21.6 gms. paraffin (m.p. 140°-145° F). To this melt was added a solution of 70 gms turpentine containing 2 gms black dye (Calco Oil Black F-4160) and the temperature of the mixture raised to about 85° C with stirring. The mixture was then allowed to cool while stirring to about 40° C before pouring into molds. The resulting paste had an acceptable, uniform consistency with good coating properties. The polish also showed good solvent retention upon standing.

EXAMPLES V – VIII

To demonstrate the versatility of the present process and the ability to vary the distribution of the high molecular weight aliphatic acids and the ratio of odd to even carbon content acids a series of ozonizations were conducted. The procedures employed were the same as those used for Example II except that minor variations in the reaction times and temperatures and catalyst levels were made. The crude mixed acid products obtained from these runs had the following compositions:

| | PRODUCT OF EXAMPLE | | | |
|---|---|---|---|---|
| | V | VI | VII | VIII |
| $C_9$-$C_{21}$ Acids | 27.4 | 11.9 | 19.1 | 16.8 |
| $C_{22}$-$C_{35}$ Acids | 63.3 | 70.9 | 71.5 | 76.7 |
| $C_{36}$ and Higher Acids | 8.1 | 9.7 | 9.5 | 8.1 |

The ratio of odd to even straight-chain acids present in the $C_{22}$-$C_{35}$ acid fraction was 2.70, 1.65, 3.04 and 1.6 for Examples V - VIII, respectively.

EXAMPLES IX – XI

Following the detailed procedure described in Example II mixed acid products were prepared by ozonizing $C_{30+}$ α-olefins at 75°-85° C followed by oxidation and scission. In these runs the ratio of α-olefin to pelargonic acid solvent was varied from 1:1 to 1:3 to determine the effect on the resulting products. Solvent ratios employed and compositions of the products obtained from these runs were as follows:

| | PRODUCT OF EXAMPLE | | |
|---|---|---|---|
| | IX | X | XI |
| Olefin:Solvent | 1:1 | 1:1.5 | 1:3 |
| $C_9$-$C_{21}$ Acids | 9.5 | 12.8 | 6.2 |
| $C_{22}$-$C_{35}$ Acids | 73.5 | 72.1 | 73.3 |
| $C_{36}$ and Higher Acids | 17.0 | 12.1 | 20.5 |
| Odd:Even Carbon Content Acids in the $C_{22}$-$C_{35}$ Range | 3.7:1 | 4:1 | 3.7:1 |

EXAMPLE XII

Repeating the procedure employed in Example I at a 3:1 solvent to olefin ratio and conducting the ozonization at 70°-75° C, 86% yield of a mixed aliphatic straight-chain acid product containing 75% $C_{22-35}$ monocarboxylic acids was obtained. The ratio of odd to even carbon content acids within the $C_{22-35}$ range was 2.9:1. When the temperature of ozonization was decreased to 55°-60° C the yield, distribution of acids and ratio of odd to even carbon content acids remained essentially the same. The reaction could not be conducted successfully at temperatures below about 50° C.

EXAMPLE XIII

Employing the procedure of Example I, except that the α-olefin feed was different, an ozonization was conducted. In this reaction the olefin feed, which by analysis was shown to be essentially all monoolefinic materials of which 80% were α-olefins, was comprised of more than 80% $C_{24}$, $C_{26}$ and $C_{28}$ olefins. The resulting mixed monocarboxylic acid product contained only 8.3% acids having chain lengths less than 22 carbon atoms with the $C_{23}$, $C_{25}$ and $C_{27}$ acids comprising 68.5% of the mixture.

EXAMPLE XIV

This example demonstrates the difference in composition of the mixed acid products of this invention as compared to the commercially available montan wax acids. A mixed acid product (identified as Sample XIV A) prepared in accordance with Example II but without being recrystallized and samples of two commercial acid waxes, identified as XIV S and XIV LP, were analyzed by gas-liquid chromatographic analysis of the methyl esters employing the procedure described in Example II. Sample XIV S (Hoechst Wax S manufactured and sold by American Hoechst Corporation) has a drop point of 78°–83° C (ASTM D566/49), congealing point 73°–77° C (ASTM D938/48), 135–155 acid value and 155–175 saponification value. Sample XIV LP (an acid wax product of American Hoechst Corporation identified as Hoechst Wax LP) has a drop point of 78°–83° C, congealing point of 75°–80° C, acid value of 115–130 and saponification value of 135–155. Acid wax S and acid wax LP are obtained by the chromic acid oxidation of crude montan wax. Results of the analysis are set forth in Table I. While the acids present in each of the Samples XIV A, XIV S and XIV LP fall within approximately the same range it is evident that the predominant acids of the chromic acid oxidized montan waxes contain an even number of carbon atoms whereas the predominant acids in the acid mixture obtained by the process of this invention contain an odd number of carbon atoms. There is a very significant difference in the distribution of the odd and even cabon content acids in the $C_{22-35}$ range where the bulk of the acids are found. The ratio of odd:even carbon content acids in the $C_{22-35}$ range for Samples XIV S and XIV LP are 0.43:1 and 0.41:1, respectively, whereas the ratio for Sample XIV A is 2.9:1.

EXAMPLE XV

To demonstrate performance differences between the mixed acids of this invention and the commercial montan wax acids of Example XIV each of the mixed acid products was reacted with tripentaerythritol employing a mol ratio of 8:1 (mixed acid:tripentaerythritol) and a temperature of about 220°–225° C to form the ester.

TABLE I

| ACID (wt %) | SAMPLE XIV A | SAMPLE XIV S | SAMPLE XIV LP | ACID (wt %) | SAMPLE XIV A | SAMPLE XIV S | SAMPLE XIV LP |
|---|---|---|---|---|---|---|---|
| $C_8$ | 0.31 | 0.03 | — | $C_{23}$ | 4.28 | 2.51 | 1.88 |
| $C_9$ | 4.49 | 0.14 | 0.04 | $C_{24}$ | 3.67 | 8.04 | 7.56 |
| $C_{10}$ | 0.61 | 0.31 | 0.08 | $C_{25}$ | 6.83 | 3.71 | 3.60 |
| $C_{11}$ | 0.92 | 0.45 | 0.19 | $C_{26}$ | 3.67 | 11.81 | 12.22 |
| $C_{12}$ | 0.61 | 0.55 | 0.47 | $C_{27}$ | 10.71 | 4.39 | 5.33 |
| $C_{13}$ | 0.71 | 0.58 | 0.31 | $C_{28}$ | 3.16 | 14.28 | 15.82 |
| $C_{14}$ | 1.02 | 0.69 | 0.27 | $C_{29}$ | 10.30 | 5.91 | 6.42 |
| $C_{15}$ | 1.43 | 1.03 | 0.82 | $C_{30}$ | 1.63 | 13.59 | 15.82 |
| $C_{16}$ | 1.68 | 1.23 | 0.67 | $C_{31}$ | 8.47 | 6.18 | 6.11 |
| $C_{17}$ | 1.73 | 1.16 | 0.51 | $C_{32}$ | 1.22 | 7.07 | 8.30 |
| $C_{18}$ | 1.94 | 1.30 | 0.82 | $C_{33}$ | 6.22 | 2.88 | 2.47 |
| $C_{19}$ | 1.99 | 1.72 | 0.86 | $C_{34}$ | 0.71 | 2.02 | 2.35 |
| $C_{20}$ | 2.60 | 1.99 | 1.09 | $C_{35}$ | 3.88 | 0.38 | 0.27 |
| $C_{21}$ | 3.01 | 1.82 | 1.02 | $C_{36}$ | 0.31 | 0.17 | 0.31 |
| $C_{22}$ | 3.36 | 3.37 | 2.47 | $C_{37+}$ | 8.82 | 0.65 | 1.61 |

The mixed acid product of this invention (XIV A) yielded a hard wax ester (AV = 15) which was an effective lubricant for processing PVC. The product was also useful as a substitute for carnauba wax in carbon paper formulations and in the formulation of shoe polishes. It was not possible to complete the esterification of acid waxes XIV S and XIV LP to the desired low acid value (< 20) since the reaction masses gelled at AV 63 and 40, respectively. It was possible, however, to obtain low AV esters without gellation by using polyols having less hydroxyl functionality, such as glycerol or ethylene glycol, with the montan wax acids.

EXAMPLE XVI

To further demonstrate the different characteristics of the mixed acid products of this invention borax emulsions were prepared and compared with identical emulsions prepared using the montan wax acids XIV S and XIV LP. 40 Parts of the mixed acid was melt blended with 20 parts synthetic Japan wax (mixed glyceride of mono- and dicarboxylic acids) and 10 parts 190/195 microcrystalline petroleum wax. The wax blend (20 grams) was then emulsified with 50 grams mineral oil, 33.5 grams water and 1.0 gram borax. Emulsions prepared using the mixed acids of this invention had good color, excellent stability and gloss, a smooth texture and were otherwise comparable to borax emulsions prepared with beeswax used in cosmetic formulations. Emulsions formed with wax acids XIV LP ranged in color from brown to tan, were grainy and generally lacked the necessary properties to be useful in cosmetic formulations. Also, the emulsion formed with wax XIV S separated after standing only a short time.

EXAMPLE XVII

An ester derived rom ethylene glycol and a mixed high molecular weight acid product of this invention was prepared. The ester had an AV of 16, hydroxyl value of 26 and melted at 75°–82° C. This ester was evaluated as a lubricant for PVC and compared with a commercial lubricant wax ester (Hoechst Wax E) derived from ethylene glycol and montan wax acids and having an AV of 15--20. The esters were incorporated into PVC homopolymer in accordance with the following recipe:

| | |
|---|---|
| PVC resin (Diamond Shamrock PVC-40) | 100 parts |
| Tin mercaptide stabilizer | 2 parts |
| Epoxidized soya | 1 part |
| Lubricant ester | 0.5 part |

The resins were milled on a conventional two-roll mill at 350° F and 10 mil sheets formed by pressing at 350° F and 500 psig for 3 minutes and 200 psig for 5 minutes. All the sheets exhibited excellent clarity. One inch squares were then oven-aged at 350° C for 80 minutes or until failure. The resin containing the commercial ester lubricant began discoloring about 10 minutes before the resin containing the ester prepared from the mixed acids of this invention. Also, the resin containing the commercial product was completely degraded (blackened) about 10 minutes earlier.

A 56 gram sample of each resin also evaluated in a Brabender plasticorder — a convenient laboratory tool to measure the flow properties of a resin with time. Fusion data was obtained at 160° C using a No. 6 roller head at a rotor speed of 60 rpm. Results were as follows:

| Lubricant | $T_s$ (Time to start of fusion) | Torque (meter grams) | $T_p$ (Time to fusion peak) | Torque (meter grams) |
|---|---|---|---|---|
| Ester prepared from acids of this invention | 9'30" | 950 | 15'45" | 2700 |
| Commercial Ester | 7'15" | 1000 | 10'00" | 3450 |
| Control (no lubricant) | 2'18" | 1640 | 5'45" | 4150 |

The resins were evaluated for dynamic thermal stability in the Brabender at a temperature of 195° C (other test conditions remained unchanged with the following results:

| Lubricant | $T_i$ (Time of initial Torque rise) | Torque | $T_{tg}$ (time to thermal degradation peak) | Torque |
|---|---|---|---|---|
| Ester prepared from acids of this invention | 25'00" | 1600 | 31'00" | 2700 |
| Commercial Ester | 14'30" | 1800 | 17'30" | 2750 |
| Unlubricated Control | 9'00" | 2150 | 12'24 | 3400 |

It is apparent from the above data that the fusion time and thermal stability of the resin lubricated with the ester derived from the acids of this inventions are significantly better than those obtained for the control resin and the commercially lubricated resin.

Resins lubricated with both esters were also evaluated for their ability to be extruded. The resin formulation employed for this purpose was as follows: 100 parts PVC, 4 parts acrylic processing aid, 2 parts tin mercaptide stabilizer, 1 part epoxidized soya and 0.5 part lubricant ester. The resins were extruded employing a Brabender machine fitted with an extrusion head model EX-200 at a screw speed of 40 rpm (¾ inch diameter, 20:1 L/D, 4:1 compression ratio screw; ¼ inch diameter rod die). The temperature in the first zone was 350° F whereas the second zone was heated to 365° F with the die temperature at 380° F. Extrusion results were as follows:

| Lubricant | Rate (lbs/hr) | Torque (meter grams) | Die Pressure (psig) |
|---|---|---|---|
| Ester prepared from acids of this invention | 4.5 | 2400 | 1250 |
| Commercial Ester | 4.7 | 3300 | 1250 |
| Unlubricated Control | 3.1 | 4800 | 2800 |

EXAMPLE XVIII

Esters were prepared using the mixed acids of Example XIV and evaluated as PVC lubricants. The polyol used for esterification was ethylene glycol. The ester of mixed acid XIV A had a final acid value of 20. Acid values of the esters of commercial wax acids XIV S and XIV LP were 23 and 20.6, respectively. When incorporated into the PVC formulations of Example XVII the respective fusion times were 13'36", 7'00" and 5'30" indicating the ester derived from the mixed acids of the present invention is a more efficient lubricant for PVC.

EXAMPLE XIX

To still further point out the advantages obtained with derivatives of the high molecular weight aliphatic straight-chain monocarboxylic acids of this invention ester-soaps were prepared for evaluation in PVC and compared with a commercially available ester-soap wax. Fusion properties were determined in accordance with the above-specified conditions. Ester-soap A was obtained by reacting 1,3-butylene glycol and calcium hydroxide with the mixed high molecular weight acid of Example II and contained 2% by weight calcium. Ester-soap B similarly contained about 2% by weight calcium and was obtained by reacting the mixed acid of Example II with calcium hydroxide and a 50/50 mixture of ethylene glycol and 1,3-butylene glycol. The partly saponified ester commercial wax (Hoechst Wax OP) contains 2% calcium and is derived from montan wax acids and a mixture of glycols, primarily 1,3-butylene glycol. Ester-soaps A and B and the commercial product were incorporated into the PVC formulation of Example XVII at a 0.5 phr level with the following results:

| Lubricant | $T_s$ | Torque | $T_p$ | Torque |
|---|---|---|---|---|
| Ester-Soap A | 18'00" | 600 | 22'15" | 3600 |
| Ester-Soap B | 15'15" | 750 | 20'00" | 3000 |
| Commercial Ester-Soap | 9'00" | 800 | 11'30" | 3250 |
| Unlubricated Control | 1'00" | 720 | 2'45" | 4200 |

We claim:
1. A process for the preparation of mixed high molecular weight aliphatic straight-chain monocarboxylic acids wherein less than 30% by weight of the acids have fewer than 22 carbon atoms, less than 20% by weight of the acids have greater than 35 carbon atoms, acids in the $C_{22-35}$ range constitute at least 55% or more of the total acid product and the ratio of odd to even carbon content acids in the $C_{22-35}$ range is between about 1.5:1 and 10:1 which comprises:
   1. reacting ozone and an olefin having from 22 to 60 carbon atoms, of which 60% or more are α-olefins, at a temperature from about 50° C to 100° C in the presence of a participating monocarboxylic acid solvent containing from about 4 to 13 carbon atoms, the weight ratio of said olefin to participating solvent ranging between about 2:1 to 1:10;
   2. treating the resulting olefin ozonide of step (1) with oxygen at a temperature from about 75° C to about 145° C to effect scission and oxidation of the ozonide to the acid products; and
   3. recovering the mixed acid product by stripping off the participating solvent at an elevated temperature and reduced pressure.
2. A mixed acid composition obtained by the process of claim 1, consisting essentially of high molecular weight aliphatic straight-chain monocarboxylic acids wherein less than 30% by weight of the acids have fewer than 22 carbon atoms, less than 20% by weight of the acids have greater than 35 carbon atoms, acids in the $C_{22-35}$ range constitute at least 55% or more of the total acid product and the ratio of odd to even carbon con- tent acids in the $C_{22-35}$ range is between about 1.5:1 and 10:1.

3. The mixed acid composition of claim 2 wherein the ratio of odd to even carbon content acids in the $C_{22-35}$ range is between about 1.75:1 and 4:1.

4. The mixed acid composition of claim 2 wherein less than 20% by weight of the acids have less than 22 carbon atoms, 70 weight percent or more of the acids are $C_{22-35}$ acids and less than 10% of the acids have more than 35 carbon atoms.

5. The composition of claim 4 wherein the ratio of odd to even carbon content acids in the $C_{22-35}$ range is between about 1.75:1 and 4:1.

6. The process of claim 1 wherein at least 60% by weight of the olefins have the formula $R'CH=CH_2$ wherein R' is an alkyl radical containing from 20 to 48 carbon atoms.

7. The process of claim 1 wherein the recovered mixed acid product is bleached with ozone and recrystallized to improve the color.

8. The process of claim 1 wherein the ozonization is conducted at a temperature from about 60° C to about 85° C and the participating solvent is at least 80% $C_{6-12}$ monocarboxylic acids.

9. The process of claim 8 wherein at least 60% by weight of the olefins have the formula $R'CH=CH_2$ wherein R' is an alkyl radical containing from 20 to 48 carbon atoms, the participating solvent is pelargonic acid or a mixture of acids containing at least 50% pelargonic acid and the weight ratio of olefin to participating solvent is between about 1:1 and 1:3.

10. The process of claim 8 wherein step (2) is conducted in a stepwise manner by first contacting the olefin ozonide with oxygen in the presence of an alkali metal hydroxide catalyst at a temperature of 85° C to 105° C and then adding a manganese compound catalyst and heating at 100° C to 125° C.

11. The process of claim 10 wherein a mixture of oxygen and ozone is employed during the initial heating period and after the manganese catalyst is added and the heating continued pure oxygen is used.

12. The process of claim 10 wherein at least 60% by weight of the olefins have the formula $R'CH=CH_2$ where R' is an alkyl radical containing from 20 to 48 carbon atoms, the participating solvent is pelargonic acid or a mixture of acids containing at least 50% pelargonic acid, the weight ratio of olefin to participating solvent is between about 1:1 and 1:3, the manganese catalyst is a manganese salt of a $C_{2-16}$ carboxylic acid and the combined catalyst ranges from 0.01% to about 2% by weight of the reaction mixture.

* * * * *